(12) United States Patent
Jobdevairakkam et al.

(10) Patent No.: US 8,575,385 B2
(45) Date of Patent: Nov. 5, 2013

(54) PROCESS OF MAKING OPTICALLY PURE MELPHALAN

(75) Inventors: Christopher N. Jobdevairakkam, Plainsboro, NJ (US); Hero Velladurai, Plainsboro, NJ (US)

(73) Assignee: Navinta LLC, Ewing, NJ (US)

( * ) Notice: Subject to any disclaimer, the term of this patent is extended or adjusted under 35 U.S.C. 154(b) by 820 days.

(21) Appl. No.: 12/408,418

(22) Filed: Mar. 20, 2009

(65) Prior Publication Data

US 2009/0240074 A1 Sep. 24, 2009

Related U.S. Application Data

(60) Provisional application No. 61/038,172, filed on Mar. 20, 2008.

(51) Int. Cl.
*C07C 229/36* (2006.01)
*C07C 51/367* (2006.01)
*C07C 51/48* (2006.01)

(52) U.S. Cl.
CPC ............. *C07C 229/36* (2013.01); *C07C 51/367* (2013.01); *C07C 51/48* (2013.01)
USPC .............................. 560/40; 562/401; 562/445

(58) Field of Classification Search
None
See application file for complete search history.

(56) References Cited

U.S. PATENT DOCUMENTS

| 2,491,926 | A | * | 12/1949 | Lorand et al. .................. 568/814 |
| 3,032,584 | A | | 5/1962 | Bergel et al. |
| 3,032,585 | A | | 5/1962 | Bergel et al. |

FOREIGN PATENT DOCUMENTS

| CN | 1011004400 | A | * | 1/2008 |
| EP | 0233733 | A2 | | 8/1987 |
| GB | 1377336 | A | | 12/1974 |
| SU | 526616 | A | * | 12/1976 |

OTHER PUBLICATIONS

Stoddart (Synthesis strategy offers no protection, Chemistry World, Mar. 2007, retrieved from http://www.rsc.org/chemistryworld/News/2007/21030701.asp on Aug. 15, 2011).*
International Search Report & Written Opinion of the International Searching Authority; PCT/US09/01810; May 18, 2009; 7 pages.
Larden, et al. "Synthesis of N-Aminoacyl Derivatives of Melphalan for Potential Use in Drug Targeting."; Tetrahedron Letters, 1996, vol. 37, pp. 7581-7582, p. 7581, para 4; p. 7582 Scheme.
Larden, et al.; Synthesis of Aminoacyl Derivatives of Melphalan for Use in Antibody Directed Enzyme Pro-drug Therapy.; Tetrahedron, 1999, vol. 55, pp. 3265-3276. p. 3273, para 3; p. 3267, scheme 1.

* cited by examiner

*Primary Examiner* — Rosalynd Keys
(74) *Attorney, Agent, or Firm* — St. Onge Steward Johnston & Reens LLC (57) ABSTRACT

This invention provides a process of making optically pure melphalan of the formula

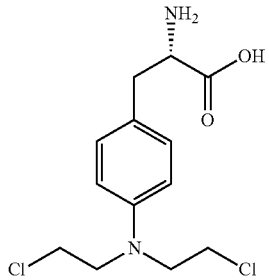

by hydroxyethylation, in a regioselective manner, of the aromatic amino group rather than the glycinic amino group.

25 Claims, 4 Drawing Sheets

FIG. 1

SCHEME - 1

(a) - Nitration using nitric acid and sulfuric acid; (b) - Glycinic amine protection ($R_2$ = acetyl, formyl, or phthaloyl) and esterification ($R_1$ = H, methyl, ethyl); (c) - Reduction of Nitro group to amino group using hydrogenation; (d)- Hydroxyethylation of aromatic amine using ethylene oxide; (e) - Chlorination using $POCl_3$ / $SOCl_2$; (f) - Resolution of racemic mixture to obtain the L-form; (g) - Deprotection and hydrolysis of ester group.

FIG. 2

SCHEME - 2

(a) - Nitration using nitric acid and sulfuric acid; (b)-Reduction of Nitro group to amino group using hydrogenation; (c) Esterification ($R_1$ = methyl, ethyl, lower alkyl); (d)- Hydroxyethylation of aromatic amine using ethylene oxide; (e) - Chlorination using $POCl_3$ / $SOCl_2$; (f) - Hydrolysis of ester group.

SCHEME - 3

(a) - Nitration using nitric acid and sulfuric acid; (b)-Reduction of Nitro group to amino group using hydrogenation; (c)- Hydroxyethylation of aromatic amine using ethylene oxide; (d) Esterification ($R_1$ = methyl, ethyl, lower alkyl); (e) - Chlorination using $POCl_3$ / $SOCl_2$; (f) - Hydrolysis of ester group.

SCHEME - 4

(a) - Nitration using nitric acid and sulfuric acid; (b)-Reduction of Nitro group to amino group using hydrogenation; (c)- Hydroxyethylation of aromatic amine using ethylene oxide; (d) Chlorination using $POCl_3$ / $SOCl_2$ (e) Base treatment

PROCESS OF MAKING OPTICALLY PURE MELPHALAN

CROSS REFERENCE TO RELATED APPLICATIONS

The present application claims the benefit under 35 U.S.C. §119 (e) of the Provisional Patent Application Ser. No. 61/038,172 filed Mar. 20, 2008.

FIELD OF THE INVENTION

The present Invention relates to a novel stereospecific synthetic process of manufacturing optically pure Melphalan.

BACKGROUND OF THE INVENTION

Melphalan is the L form of 4-(bis(2-chloroethyl)amino) phenylalanine known to exhibit antitumor activity. The D form or the racemic DL form is found to be less active than the L-form.

Invention of the molecule Melphalan was disclosed in U.S. Pat. No. 3,032,584 (Franz) and U.S. Pat. No. 3,032,585 (John) issued in 1962.

Figure 1:
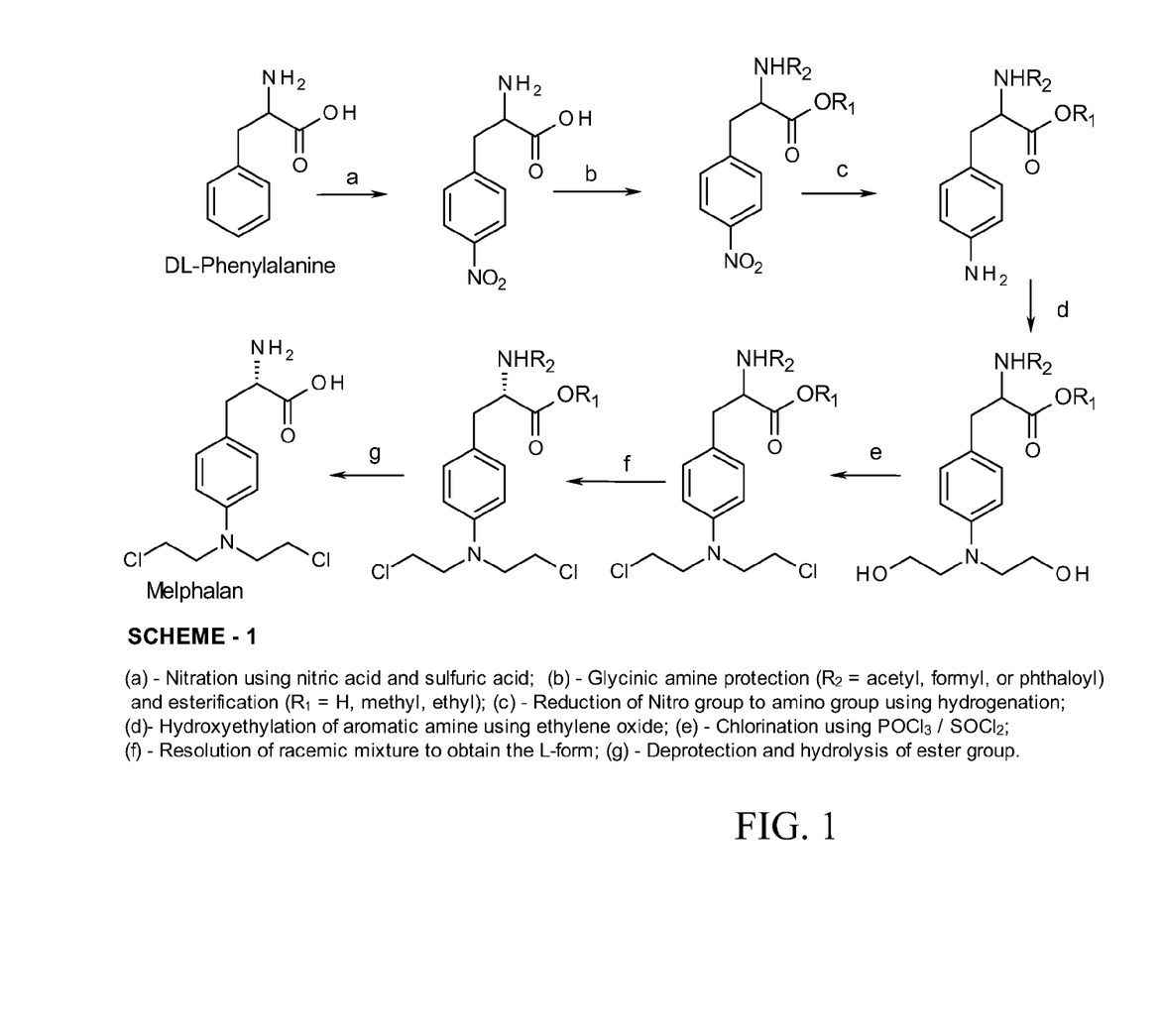
FIG. 1 is a general well-known synthetic scheme to prepare Melphalan from an intermediate, 4-aminophenylalanine, prepared from DL-phenylalanine.

Melphalan is synthesized from a key intermediate, 4-aminophenylalanine, which is prepared from L-phenylalanine. A general synthetic scheme of the synthesis of melphalan is shown in FIG. 1.

The key intermediate 4-aminophenylalanine has two active amino groups, one at the alpha carbon to the carboxylic acid function (glycinic amino group) and the other at the $4^{th}$ carbon of the phenyl ring (aromatic amino group). All the prior art processes disclose the need to protect the glycinic amino group so as to selectively introduce the hydroxyethyl or chloroethyl group on to the aromatic amino group. The protecting groups commonly used in the prior art are acetyl, formyl, and phthaloyl groups.

British patent GB1377336 discloses a process of obtaining pure L-form of 4-(bis(2-chloroethyl)amino)phenylalanine by optically resolving the DL-racemic form of the N-formyl derivative using brucine salt formation and then deprotecting the formyl group.

U.S. Pat. Nos. 3,032,584 and 3,032,585 disclose the use of having a phthaloyl group protect the glycinic amino group.

European patent EP0233733 discloses a process of making L-4-(bis(2-chloroethyl)amino) phenylalanine by using a phthalamide group to protect the glycinic amino group of a 4-nitro phenylalanine ethyl ester, and claiming an advantage over the processes disclosed in U.S. Pat. Nos. 3,032,584 and 3,032,585. This publication also discloses that a p-nitro-phthaloyl-protected intermediate (or its ethyl ester) helps in retention of optical purity.

All of the prior art examples, in one way or another, utilize a process that requires protecting the glycinic amino group to introduce the hydroxyethyl group at the aromatic amino group. In such a process, it is essential to decouple the protecting group at the end stage of the manufacturing process, which often involves aqueous hydrolysis and the encumbent generation of hydrolytic impurities which are difficult to remove. Another problem is that N-protected phenylalanine tends to racemize in the presence of an acid or base; racemization at any of the stages of making Melphalan is one of the most serious problems in the manufacture of Melphalan.

It is the prime objective of this invention to provide a chemical process of making optically pure Melphalan involving steps that does not cause racemization.

SUMMARY OF THE INVENTION

The present invention relates to a novel process of making melphalan and its intermediates in optically pure L-form. The process disclosed in this invention involves the regiospecific hydroxyethylation of the aromatic amino group without protecting the glycininc amino group of p-aminophenylalanine. The process demonstrated in this invention involves regiospecific reaction parameters to obtain 4-(bis(2-chloroethyl) amino)phenylalanine or its alkyl ester without any protection of the glycinic amino group.

More particularly, in one embodiment this invention provides a process of making 4-(bis-(2-hydroxyethyl)amino)-L-phenylalanine of the formula wherein R1 is H or a lower straight or branched chain alkyl of 1 to 6 carbons, by (a) reacting ethylene oxide with 4-amino-L-phenylalanine of the formula to obtain 4-(bis-(2-hydroxyethyl)amino)-L-phenylalanine of the formula wherein R1 is H or a lower straight or branched chain alkyl of 1 to 6 carbons; and (b) purifying the 4-(bis-(2-hydroxyethyl)amino)-L-phenylalanine obtained in step (a) with an aqueous organic solvent mixture. The purification preferably removes at least one impurity selected from 4-(bis-(2-hydroxyethyl)amino)-L-phenalanine, 4-(bis(2-hydroxyethyl) amino)phenyl)-2-(2-hydroxyethylamino)propanoic acid, and an alkyl ester of the latter.

The aqueous organic solvent mixture described in the above embodiment may be a mixture of water and one or more water miscible solvents selected from the group consisting of alcohols having not more than six carbons, acetonitrile, acetone, dioxan, or tetrahydrofuran, and a combination thereof.

The step of reacting ethylene oxide with 4-amino-L-phenylalanine of the above embodiment may occur at room temperature or at temperature in the range of from about 0° C. to about 50° C., 20° C. to 50° C., or 20° C. to 40° C. The purifying step may produce 95% chemically and optically pure 4-(bis-(2-hydroxyethyl)amino)-L-phenylalanine.

In a second embodiment, this invention provides a process of making optically pure melphalan by chlorinating a 4-(bis (2-hydroxyethyl)amino)-L-phelylalanine alkyl ester, acidifying the alkyl ester, preferably at a pH in the range of from about 2 to about 4, to yield crude melphalan, purifying the crude melphalan in an aqueous acid solution, and precipitating melphalan base at an approximately neutral pH in the range of from about 5 to about 8.5, preferably from about 6.5 to about 7.5. The alkyl ester, which is preferably methyl, ethyl, or n-propyl, can be obtain by esterifying 4-(bis(2-hydroxyethyl)amino)-L-phenylalanine with one or more alkanols, preferably having no more than about six carbons. Acidification is preferably achieved with hydrochloric, sulfuric, citric, methane sulfonic, toluene sulfonic, or acetic acid, or a compatible mixture thereof. The 4-(bis(2-hydroxyethyl)amino)-L-phenylalanine described in this embodiment may be present in the form of a free base or its acid salt.

In a third embodiment, this invention provides a process of making optically pure melphalan by chlorinating 4-(bis(2-hydroxyethyl)amino)-L-phenylalanine, which is present either in the form of a free base or its acid salt, and adjusting the pH to a pH in the range of from about 2 to about 4 to form crude 4-(bis(2-chloroethyl)amino)-L-phenylalanine (melphalan); and purifying the crude 4-(bis(2-chloroethyl) amino)-L-phenylalanine by dissolving the crude melphalan in an aqueous acid solution and precipitating out melphalan base.

In a fourth embodiment, this invention provides a process of making optically pure melphalan by chlorinating 4-(bis(2-hydroxyethyl)amino)-L-phenylalanine alkyl ester to produce crude 4-(bis(2-chloroethyl)amino)-L-phenylalanine alkyl ester; reacting said crude 4-(bis(2-chloroethyl)amino)-L-phenylalanine alkyl ester with an aqueous solution to form an acid salt of 4-(bis(2-chloroethyl)amino)-L-phenylalanine alkyl ester; hydrolyzing said 4-(bis(2-chloroethyl)amino)-L-phenylalanine alkyl ester acid salt and adjusting the pH in a pH in the range of from about 2 to about 4 to yield crude 4-(bis(2-chloroethyl)amino)-L-phenylalanine (melphalan); and purifying crude melphalan by dissolving the same in aqueous acid and precipitating the melphalan base. The 4-(bis (2-hydroxyethyl)amino)-L-phenylalanine alkyl ester described in this embodiment may be present either in the form of a free base or its acid salt.

In the second, third, and fourth embodiments, the purifying step may include dissolving melphalan in an aqueous acid mixture. The chlorination step may produce a product in the form of a base or in the form of a sulfate salt.

The aqueous acid of the second, third, and fourth embodiments is selected from the group consisting of hydrochloric acid, sulfuric acid, citric acid, methane sulfonic acid, toluene sulfonic acid, or acetic acid, and combinations thereof.

The alkyl ester described in the second and fourth embodiments may be a methyl, ethyl, or n-propyl ester, as well as other forms of esters known in the art.

The purifying step of the second, third, and fourth embodiments may occur at an approximately neutral pH, a pH in the range from about 5 to about 8.5, a pH in the range of from about 6.5 to about 7.5, or a pH in the range of from about 1 to about 3.5. The temperature of this purifying step may be a temperature in the range of from about 35° C. to about 60° C.

The temperature of the chlorinating step of the second, third, and fourth embodiments may be a temperature of from about 50° C. to about 90° C., while the hydrolyzing step of the these embodiments may occur at a temperature of about 100° C.

A fifth embodiment of the invention involves a process of making 4-(bis-(2-hydroxyethyl)amino)-L-phenylalanine of the formula wherein R1 is H or a lower straight or branched chain alkyl of 1 to 6 carbons, comprising the steps of; (a) hydroexyethylation, in a regioselective manner of the aromatic amino group of 4-amino-L-phenylalanine of the formula to obtain 4-(bis-(2-hydroxyethyl)amino)-L-phenylalanine; and (b) purifying the 4-(bis-(2-hydroxyethyl)amino)-L-phenylalanine obtained in step (a) with an aqueous organic solvent.

A sixth embodiment of the invention involves a process of making 4-amino-L-phenylalanine comprising the steps of: (a) introducing 4-nitro-L-phenylanine; and (b) hydrogenating the 4-nitro-L-phenylanine in a medium having methanol and sodium hydroxide. The medium may further have a palladium or a carbon catalyst, and it may have hydrogen gas. The hydrogenating step may be done under pressures in the range of from about 20 psi to about 100 psi.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

In general, Melphalan is synthesized from 4-amino L-phenylalanine using the process shown in FIG. 1, wherein the glycinic amino group is protected by an acetyl, formyl, or phthaloyl group. All the prior art processes involve protecting the glycinic amino group so as to direct the hydroxyethyl group to the aromatic amino group. In such a process, it is essential to decouple the protecting group at the end stage of the manufacturing process, even though this aqueous hydrolysis typically generates hydrolytic impurities that are difficult to remove. Another problem with the prior art processes is that N-protected phenylalanine is susceptible of racemization in presence of an acid or base. As previously noted, racemization at any of the process stages of making Melphalan is one of its most serious manufacturing problems.

Figure 2:
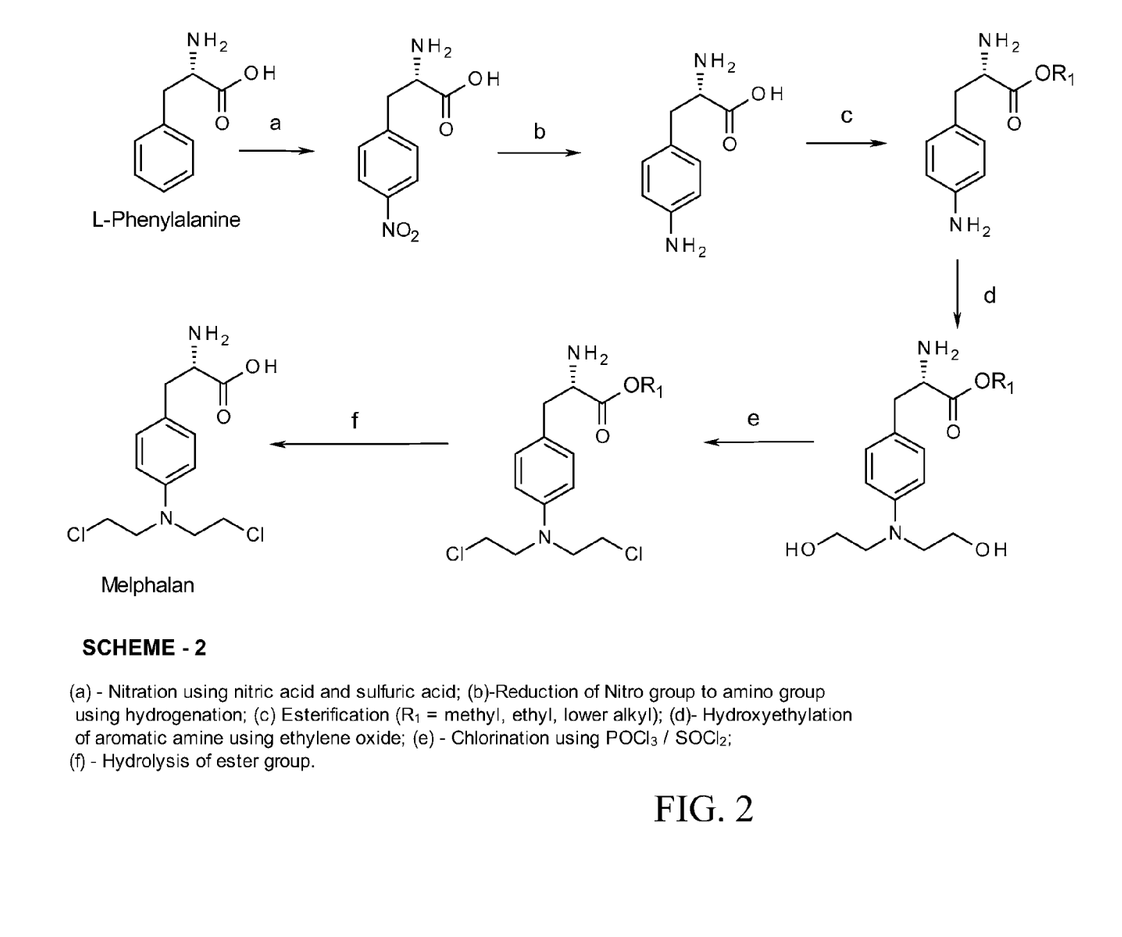
FIG. 2 is a first synthetic scheme of the present invention to prepare melphalan from an intermediate, 4-aminophenylalanine, prepared from L-phenylananine.
Figure 3:
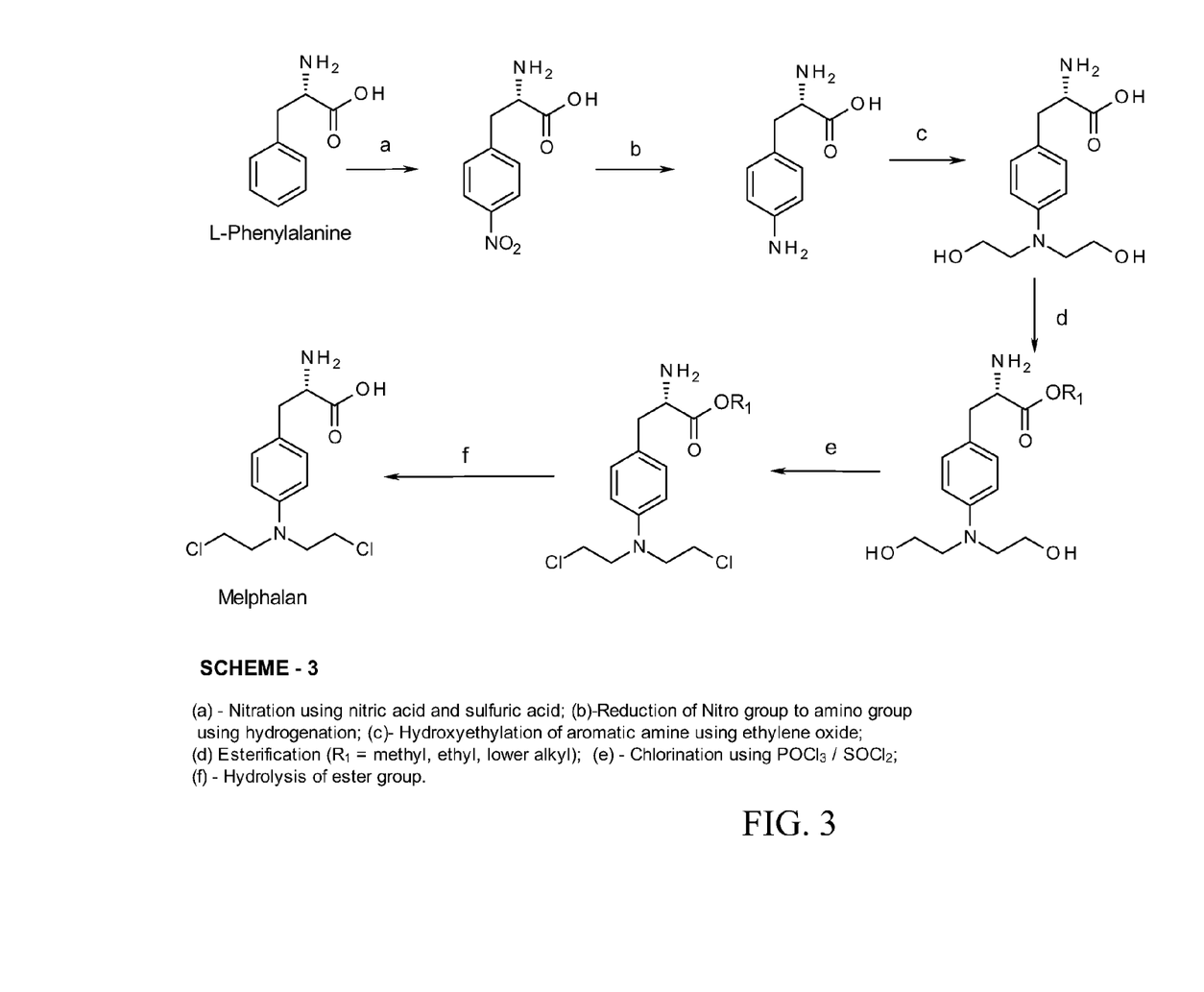
FIG. 3 is a second synthetic scheme of the present invention to prepare melphalan from an intermediate, 4-aminophenylalanine, prepared from L-phenylananine.
Figure 4:
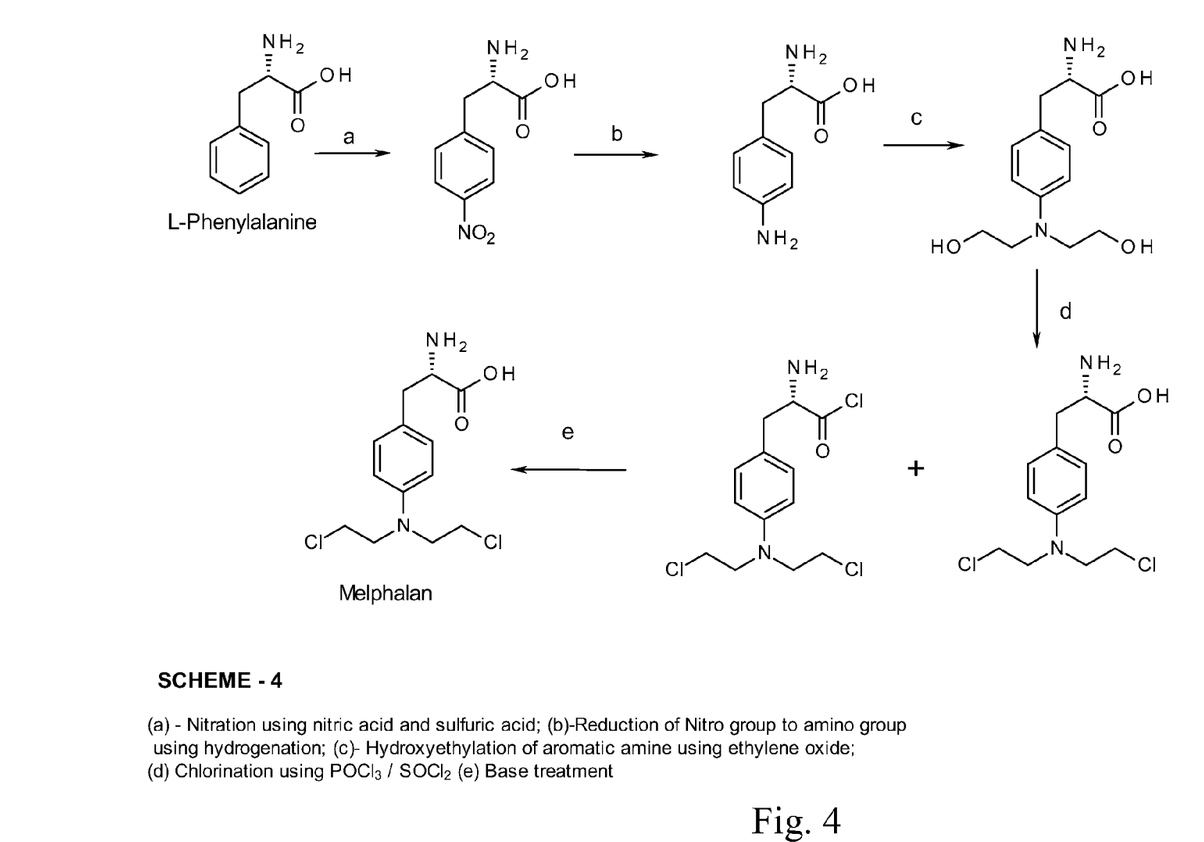
FIG. 4 is a third synthetic scheme to prepare melphalan from an intermediate, 4-aminophenylalanine, prepared from L-phenylananine, without using esterification.

None of the prior art provides any chemical process parameters that are regiospecific to perform hydroxyethylation at the aromatic amino group in 4-aminophenylalanine without using any protecting agent to block the glycinic amino group. This invention provides synthetic schemes that are improvements over the prior art for making optically pure Melphalan. (See FIGS. 2-4).

The present invention is directed to hydroxyethylation, in a regioselective manner, of the aromatic amino group rather than the glycinic amino group. Accordingly, this invention is advantageous for methods of production of melphalan and related compounds without the need for a protective group at the glycinic amino group. A further advantage of this invention is the avoidance of racemization at the carbon bearing the glycinic amino group.

According to one embodiment of this invention, 4-amino-L-phenylalanine is reacted with ethylene oxide to obtain crude 4-(bis(2-hydroxyethyl)amino)-L-phenylalanine, which is chemically purified to yield more than 95% chemically and optically pure 4-(bis(2-hydroxyethyl)amino)-L-phenylalanine; chlorination of this compound gives optically pure Melphalan.

According to another embodiment of this invention, a process of manufacture of melphalan comprises the following steps, preferably, but not necessarily, in order: (a) reacting 4-amino-L-phenylalanine with ethylene oxide at essentially ambient or room temperature, preferably at a temperature in the range of from about 20° C. to about 40° C.; (b) isolating and optionally purifying crude 4-(bis(2-hydroxyethyl)amino)-L-phenylalanine; (c) esterifying 4-(bis(2-hydroxyethyl)amino)-L-phenylalanine refluxing with lower alkyl alcohols, preferably n-$C_{1-6}$, to produce the corresponding alkyl ester; (d) chlorinating 4-(bis(2-hydroxyethyl)amino)-L-phenylalanine alkyl ester to produce 4-(bis(2-chloroethyl)amino)-L-phenylalanine alkyl ester at a temperature elevated from essentially ambient, preferably at a temperature in the range of from about 50° C. to about 90° C.; (e) hydrolyzing 4-(bis(2-chloroethyl)amino)-L-phenylalanine alkyl ester at a reflux temperature of about 100° C. to produce 4-(bis(2-chloroethyl)amino)-L-phenylalanine Melphalan; and (f) optionally purifying, isolating, and/or drying the Melphalan obtained in step (e) at a temperature essentially elevated from ambient, preferably at a temperature in the range of from about 35° C. to about 60° C.

According to another embodiment, this invention provides a process for manufacturing Melphalan, comprising the steps of: (a) reacting 4-amino-L-phenylalanine alkyl ester with ethylene oxide at essentially ambient to a slightly elevated temperature, preferably at a temperature in the range of from about 20° C. to about 50° C., and isolating and optionally purifying the crude 4-(bis(2-hydroxyethyl)amino)-L-phenylalanine alkyl ester obtained thereby; (b) chlorinating the 4-(bis(2-hydroxyethyl)amino)-L-phenylalanine alkyl ester to yield 4-(bis(2-chloroethyl)amino)-L-phenylalanine alkyl ester at an elevated temperature, preferably at a temperature in the range of from about 40° C. to about 90° C.; and (c) hydrolyzing the 4-(bis(2-chloroethyl)amino)-L-phenylalanine alkyl ester at a further elevated temperature, preferably at a temperature of about 100° C., to yield 4-(bis(2-chloroethyl)amino)-L-phenylalanine, Melphalan, and optionally purifying, isolating, and/or drying the same to produce optically pure Melphalan.

According to another embodiment of this invention, disclosed is a process of manufacture of Melphalan comprising the steps of: (a) reacting 4-amino-L-phenylalanine with ethylene oxide at essentially ambient temperature, preferably at a temperature in the range of from about 20° C. to about 50° C., to produce crude 4-(bis(2-hydroxyethyl)amino)-L-phenylalanine, and optionally isolating and purifying the same; (b) esterifying the 4-(bis(2-hydroxyethyl)amino)-L-phenylalanine with a lower alkyl alcohol at a reflux temperature of preferably at a temperature in the range of from about 50° C. to about 85° C., the lower alkanol preferably being a $C_{1-6}$ n-alkanol, to produce the alkyl ester thereof, (c) chlorinating the 4-(bis(2-hydroxyethyl)amino)-L-phenylalanine alkyl ester at an elevated temperature, preferably at a temperature in the range of from about 50° C. to about 90° C., to yield 4-(bis(2-chloroethyl)amino)-L-phenylalanine alkyl ester; (d) isolating the chlororinated product of step (c) as a salt of an acid selected from the group consisting of sulfuric acid, methane sulfonic acid, toluene sulfonic acid, citric acid, and maleic acid, and compatible mixtures thereof; and (e) hydrolyzing the salt of 4-(bis(2-chloroethyl)amino)-L-phenylalanine alkyl ester at a further elevated temperature, preferably at a temperature of about 100° C., to yield 4-(bis(2-chloroethyl)amino)-L-phenylalanine melphalan, and optionally chemically purifying, isolating, and/or drying the same to produce optically pure melphalan.

The acid used in the purification step can be hydrochloric acid, sulfuric acid, citric acid, methane sulfonic acid, toluene sulfonic acid, acetic acid, or a compatible mixture thereof. Hydrolysis of the ester is preferably at a pH in the range of from about 1 to about 3.5, more preferably from about 2.0 to about 2.5.

Also disclosed in this invention is the process of making 4-amino-L-phenylalanine by hydrogenating 4-nitro-L-phenylalanine in a medium comprising predominantly methanol, and in the presence of sodium hydroxide, using palladium on carbon catalyst and hydrogen gas. In general, hydrogenation of the 4-nitro group can be performed in a solvent under acidic or neutral conditions. However, in the case of 4-nitro-L-phenylalanine, hydrogenation performed in a neutral or acidic medium did not give pure 4-amino-L-phenylalanine, whereas hydrogenation performed under alkaline conditions gave highly pure 4-amino-L-phenylalanine (purity more than 99% with quantitative yield). Hydrogenation is done preferably under pressures ranging from essentially ambient (20 psi) to elevated (100 psi or more) in the presence of a conventional catalyst, such as 5% or 10% palladium/carbon.

Detailed experimental parameters suitable for this novel process of making melphalan are provided by the following examples, which are intended to be illustrative and not limiting of all possible embodiments of the invention.

Example-1

Process of Making 4-amino-L-phenylalanine

L-Phenylalanine was converted to 4-nitro-L-phenylalanine by a conventional nitration process known in the art. Thereafter, about 100 g of 4-nitro-L-phenylalanine was dissolved in about 600 mL of about 3.5% methanolic sodium hydroxyide solution and hydrogenated by hydrogen gas at a pressure of about 45 psi in the presence of a 5% palladium/carbon catalyst with the pH of the solution being about 11. The temperature of the reaction mixture was maintained from about 20° C. to about 40° C. The reaction mixture was periodically monitored for the completion of reaction by use of HPLC analysis. The reaction mixture was then filtered to remove the palladium/carbon catalyst and neutralized to about pH 7 with acetic acid. The neutralized filtrate was cooled to about 5° C., until 4-amino-L-phenylalanine precipitated out. The precipitate was isolated by filtration, washed with methanol and dried. (Weight 76 g, HPLC Purity 98%.)

Example-2

Process of Making 4-(bis-(2-hydroxyethyl)amino)-L-phenylalanine and Purification of 4-(bis-(2-hydroxyethyl)amino)-L-phenylalanine (a) Preparation of crude 4-(bis-(2-hydroxyethyl)amino)-L-phenylalanine About 76 g of 4-amino-L-phenylalanine obtained in Example-1 was dissolved in about 1500 mL water. Into this solution about 84 g of Ethylene oxide gas was purged over a period of about 4 hours at a temperature in the range of from about 20° C. to about 50° C. Periodically, the reaction mixture was tested by HPLC to monitor the degree of completion of the reaction as determined by the content of the in situ intermediate 4-(2-hydroxyethyl)amino)-L-phenylalanine until a level of less than about 1% 4-amino-L-phenylalanine is reached. The crude 4-(bis-(2-hydroxyethyl)amino)-L-phenylalanine was isolated by precipitation by the addition of isopropanol to the concentrated residue of the reaction mixture. The precipitated crude 4-(bis-(2-hydroxyethyl)amino)-L-phenylalanine was filtered, washed with a water-isopropanol mixture, and then dried. The purity of the crude 4-(bis-(2-hydroxyethyl)amino)-L-phenylalanine recovered was found to be about 85 to 92% by HPLC (weight, 83 g) which contains about 5 to 20% of 3-(4-(bis-(2-hydroxyethyl)amino)phenyl)-2-(2-hydroxyethylamino)-propanoic acid, and less than about 3% of 4-(2-hydroxyethyl)amino-L-phenylalanine as determined by HPLC analysis.

(b) Purification of crude 4-(bis-(2-hydroxyethyl)amino)-L-phenylalanine

Using Aqueous acetone: About 83 g of finely powdered crude 4-(bis-(2-hydroxyethyl)amino)-L-phenylalanine was suspended in aqueous acetone and stirred for about 2 hours at room temperature. The purified 4-(bis-(2-hydroxyethyl)amino)-L-phenylalanine was filtered out and washed with aqueous acetone, and dried. The impurities removed by the purification of crude 4-(bis-(2-hydroxyethyl)amino)-L-phenylalanine were 4-(2-hydroxyethyl)amino-L-phenylalanine and 3-(4-(bis-(2-hydroxyethyl)amino)phenyl)-2-(2-hydroxyethylamino)-propanoic acid (the weight of purified 4-(bis-(2-hydroxyethyl)amino)-L-phenylalanine was 59 g; its purity 98% by HPLC).

Using Aqueous Acetonitrile: About 83 g of finely powdered crude 4-(bis-(2-hydroxyethyl)amino)-L-phenylalanine was suspended in aqueous Acetonitrile and stirred for about 2 hours at room temperature. The purified 4-(bis-(2-hydroxyethyl)amino)-L-phenylalanine was filtered out and washed with aqueous Acetonitrile, and dried (the weight of purified 4-(bis-(2-hydroxyethyl)amino)-L-phenylalanine was 62 g; its purity 96% by HPLC).

Using Aqueous Isopropanol: About 83 g of finely powdered crude 4-(bis-(2-hydroxyethyl)amino)-L-phenylalanine was suspended in aqueous isopropanol and stirred for about 2 hours at room temperature. The purified 4-(bis-(2-hydroxyethyl)amino)-L-phenylalanine was filtered out and washed with aqueous isopropanol, and dried (the weight of purified 4-(bis-(2-hydroxyethyl)amino)-L-phenylalanine was 55 g, its purity 99% by HPLC).

Example-3

Process of making 4-(bis-(2-hydroxyethyl)amino)-L-phenylalanine Methyl Ester

About 60 g of dried and purified 4-(bis-(2-hydroxyethyl)amino)-L-phenylalanine was mixed with 1500 mL of methanol. The reaction mass was dehydrated by distilling out about 20% of methanol. To the dry reaction mixture about 300 g of dry hydrochloric acid gas was purged in. The reaction mass was warmed to a temperature of about 65° C. and the reaction was promoted by removing the water formed in the reaction by distillation. The progress of the reaction was monitored by HPLC analysis. Upon completion of esterification, the reaction mass was neutralized with sodium bicarbonate and the precipitated inorganic salt was isolated by filtration. The filtrate was collected, concentrated by distillation, and dehydrated to a thick mass. (the weight of reaction mass residue was 60 g, its purity 96%.)

Example-4

Process of Making 4-(bis-(2-hydroxyethyl)amino)-L-phenylalanine Ethyl Ester

About 60 g of dried and purified 4-(bis-(2-hydroxyethyl)amino)-L-phenylalanine was mixed with 1500 mL of ethanol. The reaction mass was dehydrated by distilling out about 20% of ethanol. To the dry reaction mixture about 300 g of dry hydrochloric acid gas was purged in. The reaction mass was warmed to a temperature of about 80° C. and the reaction was promoted by removing water formed during the reaction by distillation. The progress of the reaction was monitored by HPLC analysis. Upon completion of esterification, the reaction mass was neutralized with sodium bicarbonate and the precipitated inorganic salt was removed and washed with ethanol. The filtrate was collected, concentrated by distillation, and dehydrated to a thick mass. (the weight of reaction mass residue was 69 g; purity 95%.)

Example-5

Process of making 4-(bis-(2-hydroxyethyl)amino)-L-phenylalanine n-propyl Ester The procedure as described in Example 4 was used, replacing the ethanol with Isopropanol. (the weight of propyl ester was 71 g; its purity 90%).

Example-6 (a)

Process of making 4-(bis-(2-chloroethyl)amino)-L-phenylalanine (Melphalan) from 4-(bis-(2-hydroxyethyl)amino)-L-phenylalanine About 60 g of dried and purified 4-(bis-(2-hydroxyethyl)amino)-L-phenylalanine was mixed with 500 mL of Acetonitrile, and then about 200 mL of Acetonitrile was distilled out from the mixture to dehydrate the reaction mixture. To the dehydrated (anhydrous) reaction mixture was added about 85 mL of phosphorous oxychloride at room temperature and the reaction mass was refluxed for about 2 hours. The progress of the reaction was monitored by HPLC. The reaction product was obtained ultimately by removing Acetonitrile from the mixture by distillation. (the weight of reaction mass residue was 40 g; its purity 80%.)

Example-6 (b)

Process of making 4-(bis-(2-chloroethyl)amino)-L-phenylalanine (Melphalan) from 4-(bis-(2-hydroxyethyl)amino)-L-phenylalanine About 60 g of dried and purified 4-(bis-(2-hydroxyethyl)amino)-L-phenylalanine was mixed with 120 mL of toluene and stirred for 10 minutes at 25° C. Thereafter, 60 mL of $POCl_3$ at 25° C. was added and the mixture was warmed to 70° C.; the reaction was monitored by HPLC (to less than 0.5% and the monochloro derivative to less than 0.5%). Upon completion, the mixture was cooled to a temperature in the range of from about 0° C. to about 5° C., about 14 g of concentrated sulfuric acid was added, and the mixture was stirred for about 45 min at that reduced temperature in the range of from about 0° C. to about 5° C. About 120 mL ethyl acetate was added to precipitate with the mixture maintained at 0 to 5° C. The precipitated sulfate salt of (2S)-2-(amino)-3-{4-[bis(2-chloroethyl)amino]phenyl}propanoic acid was filtered and then washed with ethyl acetate previously cooled to 0° C. (the weight of reaction mass residue was 45 g; its purity 96%.)

Example-7 (a)

Process of chlorination of 4-(bis-(2-hydroxyethyl)amino)-L-phenylalanine Ethyl Ester Starting with the procedure described for Example-4, about 200 mL of Acetonitrile was added to the thick residue obtained in Example-4 to dissolve the residue. To this solution was added about 85 mL of phosphorous oxychloride at room temperature and the reaction mass was refluxed for about 2 hours. The progress of the reaction was monitored by HPLC. The reaction product (4-(bis-(2-hydroxyethyl)amino)-L-phenylalanine ethyl ester) was obtained by removing Acetonitrile via distillation. (the weight of reaction mass residue was 72 g; its purity 90%.)

Example-7 (b)

Process of chlorination of 4-(bis-(2-hydroxyethyl)amino)-L-phenylalanine Methyl Ester To the thick residue obtained in Example-3 was added 120 mL of toluene and the mixture was stirred for 10 minutes at 25° C. Then 60 mL of $POCl_3$ at 25° C. was added and the mixture was warmed to 70° C.; the reaction was monitored by HPLC (less than 0.5% and monochloro derivative less than 0.5%). Upon completion, the mixture was cooled to a temperature in the range of from about 0° C. to about 5° C., about 13 g of concentrated sulfuric acid was added, and the mixture was stirred for about 45 min at a temperature in the range of from about 0° C. to about 5° C. Two liters of ethyl acetate were added while maintaining the temperature in the range of from about 0° C. to about 5° C. The precipitated sulfate salt of methyl (2S)-2-(amino)-3-{4-[bis(2-chloroethyl)amino]phenyl}propanoate was filtered and washed with ethyl acetate previously cooled to 0° C.

Example-7 (c)

Process of chlorination of 4-(bis-(2-hydroxyethyl)amino)-L-phenylalanine Methyl Ester To the thick residue obtained in Example-3, 120 mL of $POCl_3$ at 25° C. was added and the mixture stirred to make a uniform slurry. The mass was warmed to a temperature in the range of from about 60° C. to about 65° C., at which time the temperature rose due to the exothermic nature of the reaction and was maintained at a temperature of about 75° C. by using chilled water circulation; as before, the extent of reaction was determined by HPLC. At the end of reaction, about 60% of the $POCl_3$ was removed by vacuum at 70° C. The mixture was then cooled to a temperature in the range of from about 0° C. to about 5° C. About 13 g of concentrated sulfuric acid was added and the mixture stirred for about 45 min at that reduced temperature. 25 mL of ethyl acetate was added. The reduced temperature was maintained. Filtering yielded the precipitated sulfate salt of methyl (2S)-2-(amino)-3-{4-[bis(2-chloroethyl)amino]phenyl}propanoate, which was washed with ethyl acetate previously cooled to 0° C.

Example-7 (d)

Process of chlorination of 4-(bis-(2-hydroxyethyl)amino)-L-phenylalanine methyl ester To the thick residue obtained in Example-3 was added 150 g of $SOCl_2$ at 25° C. with stirring to make a uniform slurry. The reaction mass was warmed to a temperature in the range of from about 60° C. to about 65° C., at which time the exothermic reaction progressed, and the reaction mass was maintained at about 75° C. through the use of chilled water circulation and the reaction progress monitored by HPLC (less than 0.5% and monochloro derivative less than 0.5%). After reaction, the mass was cooled to a temperature in the range of from about 0° C. to about 5° C., and 25 mL ethyl acetate was added while maintaining that reduced temperature. Filtering the precipitate gave methyl (2S)-2-(amino)-3-{4-[bis(2-chloroethyl)amino]phenyl}propanoate, which was washed with ethyl acetate previously cooled to 0° C.

Example-8

Process of Preparation of 4-(bis-(2-chloroethyl)amino)-L-phenylalanine (melphalan) by Hydrolysis of 4-(bis-(2-chloroethyl)amino)-L-phenylalanine Methyl/Ethyl Ester To the thick residue obtained in Example-7 (from part a, b, c, or d) or example-12 (below) about 400 mL of concentrated hydrochloric acid was added and the mixture was refluxed for about 3 hours. Completion of ester hydrolysis was monitored by HPLC analysis. The reaction mass was concentrated by distillation under vacuum to about 75% of its original volume. The concentrated mass was cooled to a temperature of about 10° C. and diluted with about 750 mL of water. Upon adjusting the pH to 2, the precipitate formed and was obtained. The precipitated crude melphalan was isolated by filtration and washed with water.

Example-9

Purification of Melphalan

The crude Melphalan obtained in any of Examples 6(a), 6(b), or 8 was further purified by dissolution in aqueous hydrochloric acid, treated with activated carbon, and re-precipitated by adjusting the pH to about 7 with sodium acetate. The precipitated pure Melphalan was isolated by filtration, washed with aqueous methanol, and then dried under vacuum at a temperature in the range of from about 30° C. to about 45° C. (The weight of pure Melphalan was 23 g; its purity 99%.)

Example-10

Process of Making 4-amino L-phenylalanine Ethyl Ester

About 40 g of dried L-4-amino phenylalanine was mixed with 1000 mL of ethanol. The reaction mass was dehydrated by distilling out about 20% of the ethanol added. To the dried reaction mixture about 300 g of dry hydrochloric acid gas was purged in. The reaction mass was warmed to about 80° C. and the reaction was promoted by removing condensation (water formed in the reaction) by distillation. The progress of the reaction was monitored by HPLC analysis. Upon completion of the esterification reaction, the reaction mass was neutralized with sodium bicarbonate and the precipitated inorganic salt was removed, isolated, washed with ethanol, and the filtrate was collected. The filtrate was concentrated by distillation and dehydrated to a thick mass. (the weight of reaction mass residue was 41 g; its purity 98%.)

Example-11

Preparation of 4-(bis-(2-hydroxyethyl)amino)-L-phenylalanine ethyl ester

About 41 g of 4-amino-L-phenylalanine ethyl ester obtained using the procedure described in Example-10 was added to about 1200 mL water. Into this mixture about 65 g of ethylene oxide gas was purged over a period of about 4 hours at a temperature in the range of from about 20° C. to about 50° C. Periodically the reaction mixture was tested by HPLC to monitor the completion of the reaction, as determined by the content of the in situ intermediate 4-(2-hydroxyethyl)amino)-L-phenylalanine ethyl ester until a level of less than about 1% 4-(2-hydroxyethyl)amino)-L-phenylalanine ethyl ester was reached. The crude 4-(bis-(2-hydroxyethyl)amino)-L-phenylalanine ethyl ester was isolated by evaporation of solvent. The purity of 4-(bis-(2-hydroxyethyl)amino)-L-phenylalanine ethyl ester was found to be about 90% by HPLC (weight, 38 g).

Example-12

Process of making 4-(bis-(2-chloroethyl)amino)-L-phenylalanine ethyl ester from 4-(bis-(2-hydroxyethyl)amino)-L-phenylalanine ethyl ester The product 4-(bis-(2-hydroxyethyl)amino)-L-phenylalanine ethyl ester obtained from the procedure described in Example-11 was mixed with 120 mL of toluene and stirred for about 10 minutes at 25° C., whereupon 60 mL of $POCl_3$ at 25° C. was added and the mixture was warmed to 70° C. The reaction was monitored by HPLC (until less than 0.5% and monochloro derivative was less than 0.5%), whereafter it was cooled to a temperature in the range of from about 0° C. to about 5° C. 120 mL ethyl acetate was added while maintaining the reduced temperature in the range of from about 0° C. to about 5° C. Filtering the precipitate gave (2S)-2-(amino)-3-{4-[bis(2-chloroethyl)amino]phenyl} propanoic acid ethyl ester. (the weight of reaction mass residue was 36 g, its purity 98%.)

While the invention has been specifically described in connection with certain specific embodiments thereof, it is to be understood that this is by way of illustration and not of limitation and that various changes and modifications in form and details can be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:
1. A process of making 4-(bis-(2-hydroxyethyl)amino)-L-phenylalanine of the formula wherein R1 is H or a lower straight or branched chain alkyl of 1 to 6 carbons, comprising the steps of;
(a) reacting a predetermined amount of ethylene oxide, with 4-amino-L-phenylalanine of the formula wherein R1 is H or a lower straight or branched chain alkyl of 1 to 6 carbons, to obtain 4-(bis-(2-hydroxyethyl)amino)-L-phenylalanine of the formula wherein R1 is H or a lower straight or branched chain alkyl of 1 to 6 carbons; and
(b) purifying the 4-(bis-(2-hydroxyethyl)amino)-L-phenylalanine obtained in step (a) with an aqueous organic solvent mixture.

2. The process of claim 1, wherein the step of purifying removes (4-(bis-(2-hydroxyethyl)amino)phenyl)-2-(2-hydroxyethylamino)-propanoic acid, an alkyl ester thereof, or a combination of both.

3. The process of claim 1, wherein step (a) is performed in water or an aqueous organic solvent mixture.

4. The process of claim 1, wherein said aqueous organic solvent mixture is a mixture of water and one or more water miscible solvents selected from the group consisting of alcohols having not more than six carbons, acetonitrile, acetone, dioxan, or tetrahydrofuran, and a combination thereof.

5. The process of claim 3, wherein said aqueous organic solvent mixture is a mixture of water and one or more water miscible solvents selected from the group consisting of alcohols having not more than six carbons, acetonitrile, acetone, dioxan, or tetrahydrofuran, and a combination thereof.

6. The process of claim 1 wherein the purifying step produces at least 95% chemically and optically pure 4-(bis-(2-hydroxyethyl)amino)-L-phenylalanine.

7. The process of claim 1, wherein step (a) occurs at room temperature.

8. The process of claim 1, wherein step (a) occurs at a temperature in the range of about 0° C. to about 50° C.

9. The process of claim 1, wherein step (a) occurs at a temperature in the range of about 20° C. to 50° C.

10. The process of claim 1, wherein step (a) occurs at a temperature in the range of about 20° C. to 40° C.

11. A process of making optically pure melphalan, comprising the steps of:
(a) esterifying 4-(bis(2-hydroxyethyl)amino)-L-phenylalanine manufactured from the process in accordance with claim 1 with one or more alkyl alcohols to form an alkyl ester thereof;
(b) chlorinating the 4-(bis(2-hydroxyethyl)amino)-L-phenylalanine alkyl ester to yield 4-(bis(2-chloroethyl)amino)-L-phenylalanine alkyl ester;
(c) hydrolyzing the 4-(bis(2-chloroethyl)amino)-L-phenylalanine alkyl ester and adjusting the pH to a pH in the range of from about 2 to about 4 to yield crude 4-(bis(2-chloroethyl)amino)-L-phenylalanine (Melphalan);
(d) purifying the crude melphalan by dissolving the same in an aqueous acid solution and precipitating a melphalan base from the melphalan and aqueous acid solution.

12. The process of claim 11, wherein the acid is selected from the group consisting of hydrochloric acid, sulfuric acid, citric acid, methane sulfonic acid, toluene sulfonic acid, or acetic acid, and combinations thereof.

13. The process of claim 11, wherein the alkyl ester is selected from the group consisting of methyl, ethyl, or n-propyl ester, or a combination thereof.

14. A process of making optically pure melphalan, comprising the steps:
(a) chlorinating 4-(bis(2-hydroxyethyl)amino)-L-phenylalanine manufactured from the process in accordance with claim 1 and adjusting the pH to a pH in the range of from about 2 to about 4 to form crude 4-(bis(2-chloroethyl)amino)-L-phenylalanine (melphalan);
(b) purifying the crude 4-(bis(2-chloroethyl)amino)-L-phenylalanine by dissolving the crude melphalan in an aqueous acid solution and precipitating out melphalan base.

15. The process of claim 14, wherein the acid is selected from the group consisting of hydrochloric acid, sulfuric acid, citric acid, methane sulfonic acid, toluene sulfonic acid, or acetic acid, and combinations thereof.

16. A process of making optically pure Melphalan, comprising the steps:
(a) chlorinating 4-(bis(2-hydroxyethyl)amino)-L-phenylalanine alkyl ester to produce crude 4-(bis(2-chloroethyl)amino)-L-phenylalanine alkyl ester;
(b) reacting said crude 4-(bis(2-chloroethyl)amino)-L-phenylalanine alkyl ester with an aqueous solution to form an acid salt of 4-(bis(2-chloroethyl)amino)-L-phenylalanine alkyl ester;
(c) hydrolyzing said 4-(bis(2-chloroethyl)amino)-L-phenylalanine alkyl ester acid salt and adjusting the pH to a pH in the range of from about 2 to about 4 to yield crude 4-(bis(2-chloroethyl)amino)-L-phenylalanine (melphalan); and
(d) purifying crude melphalan by dissolving the same in an aqueous acid solution and precipitating the melphalan base.

17. The process of claim 16, wherein the acid is selected from the group consisting of hydrochloric acid, sulfuric acid, citric acid, methane sulfonic acid, toluene sulfonic acid, or acetic acid, and combinations thereof.

18. The process of claim 16, wherein the alkyl ester is selected from the group consisting of methyl, ethyl, or n-propyl ester, or a combination thereof.

19. A process of making 4-(bis-(2-hydroxyethyl)amino)-L-phenylalanine of the formula wherein R1 is H or a lower straight or branched chain alkyl of 1 to 6 carbons, comprising the steps of;
(a) hydroxyethylation, in a regioselective manner of the aromatic amino group of 4-amino-L-phenylalanine of the formula where R1 is H or a lower straight or branched chain alkyl of 1 to 6 carbons, to obtain 4-(bis-(2-hydroxyethyl)amino)-L-phenylalanine; and
(b) purifying the 4-(bis-(2-hydroxyethyl)amino)-L-phenylalanine obtained in step (a) with an aqueous organic solvent.

20. The process of claim 1, further comprising the steps of:
(a) introducing 4-nitro-L-phenylanine; and
(b) hydrogenating the 4-nitro-L-phenylanine in a medium having methanol and sodium hydroxide to prepare 4-amino-L-phenylalanine of the formula, wherein R1 is H or a lower straight or branched chain alkyl of 1 to 6 carbons, prior to the step of reacting with ethylene oxide.

21. The process of claim 20, wherein said medium further has a palladium on a carbon catalyst and hydrogen gas.

22. The process of claim 20, wherein the hydrogenating step is done under pressures in the range of from about 20 psi to about 100 psi.

23. The process of claim 1, wherein the 4-(bis-(2-hydroxyethyl)amino)-L-phenylalanine obtained in step (a) is precipitated by the additional of isopropanol prior to step (b).

24. The process of claim 1, wherein said predetermined amount of ethylene oxide is about 84 g for every 76 g of the 4-amino-L-pheylalanine.

25. A process of making 4-(bis-(2-hydroxyethyl)amino)-L-phenylalanine of the formula wherein R1 is H or a lower straight or branched chain alkyl of 1 to 6 carbons, comprising the steps of;
(a) dissolving 4-amino-L-phenylalanine of the formula wherein R1 is H or a lower straight or branched chain alkyl of 1 to 6 carbons, in water;
(b) reacting a predetermined amount of ethylene oxide with said 4-amino-L-phenylalanine dissolved in water obtained in step (a) to obtain 4-(bis-(2-hydroxyethyl)amino)-L-phenylalanine of the formula wherein R1 is H or a lower straight or branched chain alkyl of 1 to 6 carbons; and
(c) purifying the 4-(bis-(2-hydroxyethyl)amino)-L-phenylalanine obtained in step (b) with an aqueous organic solvent mixture.

* * * * *